US012778265B2

(12) United States Patent
Barbarino et al.

(10) Patent No.: US 12,778,265 B2
(45) Date of Patent: Nov. 3, 2026

(54) DEVICE ADJUSTMENT SYSTEM FOR A COSMETIC DEVICE CONFIGURED FOR USERS WITH LIMITED MOBILITY

(71) Applicant: L'OREAL, Paris (FR)

(72) Inventors: Casey Barbarino, San Anselmo, CA (US); Hyosik Dennis Min, Palisades Park, NJ (US)

(73) Assignee: L'OREAL, Paris (FR)

( * ) Notice: Subject to any disclaimer, the term of this patent is extended or adjusted under 35 U.S.C. 154(b) by 666 days.

(21) Appl. No.: 18/362,446

(22) Filed: Jul. 31, 2023

(65) Prior Publication Data

US 2025/0040683 A1 Feb. 6, 2025

(51) Int. Cl.
*A45D 40/00* (2006.01)
*A45D 34/00* (2006.01)
(Continued)

(52) U.S. Cl.
CPC ............. *A45D 40/00* (2013.01); *A45D 34/00* (2013.01); *A61F 4/00* (2013.01); *A45D 2200/10* (2013.01);
(Continued)

(58) Field of Classification Search
CPC .... A45D 2200/10; A45D 34/00; A45D 40/00; A45D 44/00; A47G 2400/08; A61B 5/1101; A61F 4/00
See application file for complete search history.

(56) References Cited

U.S. PATENT DOCUMENTS 5,107,870 A * 4/1992 Beck ........................ A46B 3/18 132/218
9,925,034 B2 3/2018 Pathak
(Continued)

FOREIGN PATENT DOCUMENTS

AU 2016273988 B1 10/2017
CA 2 951 338 C 12/2016
(Continued)

OTHER PUBLICATIONS

French Preliminary Search Report and Written Opinion issued May 21, 2024, in French Application No. 2311346.

*Primary Examiner* — Kidest Worku
(74) *Attorney, Agent, or Firm* — Womble Bond Dickinson (US) LLP

(57) ABSTRACT

A device adjustment system for a cosmetic device configured for users with limited mobility includes a motion stabilizer handle; a first cosmetic adapter attached to a first end of the motion stabilizer handle; a second cosmetic adapter attached to a second end of the motion stabilizer handle; and an adjustable coupler disposed in the motion stabilizer handle, the adjustable coupler including a first motion adjustment group, a second motion adjustment group, and processing circuitry, the adjustable coupler being adjustably translated between the first end and the second end of the motion stabilizer handle, the first motion adjustment group configured to couple with the first cosmetic adapter, the second motion adjustment group configured to couple with the second cosmetic adapter, and the processing circuitry configured to adjust a coupling of the adjustable coupler based on the arrangement of the motion stabilizer handle.

20 Claims, 7 Drawing Sheets

(51) Int. Cl.
*A61F 4/00* (2006.01)
*A61B 5/11* (2006.01)

(52) U.S. Cl.
CPC ......... *A47G 2400/08* (2013.01); *A61B 5/1101* (2013.01)

(56) References Cited

U.S. PATENT DOCUMENTS

| | | | | |
|---|---|---|---|---|
| 10,070,807 | B2 | 9/2018 | Shoeb et al. | |
| 10,159,428 | B1 | 12/2018 | Shoeb et al. | |
| 10,159,432 | B1 | 12/2018 | Pathak et al. | |
| 10,532,465 | B2 | 1/2020 | Pathak et al. | |
| 11,369,500 | B2 | 6/2022 | Pathak et al. | |
| 11,883,342 | B2 | 1/2024 | Pathak et al. | |
| 11,944,216 | B2 | 4/2024 | Pathak | |
| 12,035,796 | B1 * | 7/2024 | Lockhart | A45D 33/006 |
| 2012/0067364 | A1 * | 3/2012 | Wong | A45D 44/005 132/200 |
| 2020/0085168 | A1 | 3/2020 | Pang et al. | |
| 2021/0298982 | A1 | 9/2021 | Pathak et al. | |
| 2022/0095775 | A1 * | 3/2022 | Lee | A46B 13/02 |

FOREIGN PATENT DOCUMENTS

| | | | |
|---|---|---|---|
| CN | 108201477 | A | 6/2018 |
| EP | 3 332 694 | A1 | 6/2018 |
| EP | 3 463 000 | B1 | 8/2023 |
| JP | 2018-099155 | A | 6/2018 |
| KR | 10-1891409 | B1 | 8/2018 |
| WO | WO 2016/209368 | A9 | 12/2016 |

* cited by examiner

DEVICE ADJUSTMENT SYSTEM FOR A COSMETIC DEVICE CONFIGURED FOR USERS WITH LIMITED MOBILITY

FIELD

The present disclosure describes a system and features related to a device for modifying, mitigating, altering, reducing, compensation for, or the like, the movement of a cosmetic applicator caused by unintentional movements, tremors, limited mobility, or the like of a user.

BACKGROUND

Unintentional movements of the human body, or human tremors, can occur in individuals suffering from motion disorders or even healthy individuals. Due to these unintentional movements, a person may have difficulty in performing a task that requires care and precision, such as applying a cosmetic composition to a part of the body, such as the face, hands, or feet.

Therefore, there is a need for a solution that allows application of a cosmetic composition that is compatible with the diverse and disposable nature of cosmetic applicators.

SUMMARY

In one embodiment, the present disclosure relates to a device adjustment system for a cosmetic device configured for users with limited mobility, including a motion stabilizer handle; a first cosmetic adapter attached to a first end of the motion stabilizer handle; a second cosmetic adapter attached to a second end of the motion stabilizer handle; and an adjustable coupler disposed in the motion stabilizer handle, the adjustable coupler including a first motion adjustment group, a second motion adjustment group, and processing circuitry, the adjustable coupler being adjustably translated between the first end and the second end of the motion stabilizer handle, the first motion adjustment group configured to couple with the first cosmetic adapter and manipulate a motion of the first cosmetic adapter, the second motion adjustment group configured to couple with the second cosmetic adapter and manipulate a motion of the second cosmetic adapter, the processing circuitry configured to determine an arrangement of the motion stabilizer handle and instruct a motor disposed in the motion stabilizer handle and mechanically connected to the adjustable coupler to adjust a coupling of the adjustable coupler based on the arrangement of the motion stabilizer handle.

In an embodiment, the device further includes a hinge portion attached to the first end of the motion stabilizer handle, the first cosmetic adapter being attached to the hinge portion at the first end of the motion stabilizer handle.

In an embodiment, the first motion adjustment group includes an x-axis motive element and a y-axis motive element configured to maintain a level position of the first cosmetic adapter in response to manipulation of the motion stabilizer handle that arranges the motion stabilizer handle in a non-level arrangement.

In an embodiment, the second motion adjustment group includes an electromagnetic positioner configured to maintain a same position of the second cosmetic adapter in free space in response to manipulation of the motion stabilizer handle with random oscillating motions.

In an embodiment, the electromagnetic positioner includes magnetic cores arrayed around a non-magnetic tube filled with a magnetic fluid, each of the magnetic cores surrounded by windings, the magnetic cores controlled via the processing circuitry to generate a variable magnetic field that acts upon and displaces the magnetic fluid to adjust the second cosmetic adapter.

In an embodiment, upon coupling the adjustable coupler to the first cosmetic adapter, the adjustable coupler is not coupled to the second cosmetic adapter.

In an embodiment, the processing circuitry is configured to upon determining the first end of the motion stabilizer handle is vertically elevated compared to the second end of the motion stabilizer handle and the first cosmetic adapter is attached to the first end of the motion stabilizer handle, instruct the motor to adjust the adjustable coupler towards the first end of the motion stabilizer handle to couple the first motion adjustment group with the first cosmetic adapter.

In an embodiment, the processing circuitry is configured to upon determining the second end of the motion stabilizer handle is vertically elevated compared to the first end of the motion stabilizer handle and the second cosmetic adapter is attached to the second end of the motion stabilizer handle, instruct the motor to adjust the adjustable coupler towards the second end of the motion stabilizer handle to couple the second motion adjustment group with the second cosmetic adapter.

In an embodiment, the processing circuitry is configured to upon determining the first end of the motion stabilizer handle is vertically elevated compared to the second end of the motion stabilizer handle and the second cosmetic adapter is attached to the first end of the motion stabilizer handle via a radiofrequency identification (RFID) reader disposed at the second end of the motion stabilizer handle, instruct the motor to adjust the adjustable coupler towards the first end of the motion stabilizer handle to couple the second motion adjustment group with the second cosmetic adapter.

In an embodiment, the device further includes a strap attached to a rotating platform, the rotating platform connected to the motion stabilizer handle via a rotating post, a rotation axis of the rotating post being orthogonal to a length axis of the motion stabilizer handle, the strap configured to secure an object to the rotating platform and the motion stabilizer handle.

In an embodiment, the adjustable coupler includes an accelerometer electrically connected to the processing circuitry.

In an embodiment, the adjustable coupler includes a gyroscope electrically connected to the processing circuitry.

The present disclosure additionally relates to a method of adjusting an adjustable coupler in a cosmetic device configured for users with limited mobility, including determining, via processing circuitry disposed in a motion stabilizer handle of the cosmetic device, an arrangement of the motion stabilizer handle, the motion stabilizer handle including a first cosmetic adapter attached to a first end of the motion stabilizer handle and a second cosmetic adapter attached to a second end of the motion stabilizer handle, the adjustable coupler including a first motion adjustment group, a second motion adjustment group, and the processing circuitry, the adjustable coupler being adjustably translated between the first end and the second end of the motion stabilizer handle, the first motion adjustment group configured to couple with the first cosmetic adapter and manipulate a motion of the first cosmetic adapter, the second motion adjustment group configured to couple with the second cosmetic adapter and manipulate a motion of the second cosmetic adapter, the processing circuitry configured to determine an arrangement of the motion stabilizer handle and instruct a motor disposed in the motion stabilizer handle and mechanically connected to the adjustable coupler to adjust a coupling of the adjustable coupler based on the arrangement of the motion stabilizer handle; and upon determining the first end of the motion stabilizer handle is vertically elevated compared to the second end of the motion stabilizer handle and the first cosmetic adapter is attached to the first end of the motion stabilizer handle, instruct, via the processing circuitry, the motor to adjust the adjustable coupler towards the first end of the motion stabilizer handle to couple the first motion adjustment group with the first cosmetic adapter

BRIEF DESCRIPTION OF THE DRAWINGS

A more complete appreciation of the embodiments and many of the attendant advantages thereof will be readily obtained as the same becomes better understood by reference to the following detailed description when considered in connection with the accompanying drawings, wherein.

DETAILED DESCRIPTION

The present disclosure describes a cosmetic applicator system that minimizes, modifies, mitigates, alters, reduces, compensates for, or the like unintentional movements by stabilizing, orienting, operating, controlling, etc. an applicator for a user and is also designed to be flexible to accommodate different types of commercially available cosmetic applications. The present disclosure further describes a system and features to enhance the functionality of such a cosmetic applicator system.

The basic features and operation of a motion stabilizing device for a cosmetic applicator is described in U.S. Pat. No. 11,458,062, which is incorporated herein by reference.

Figure 1:
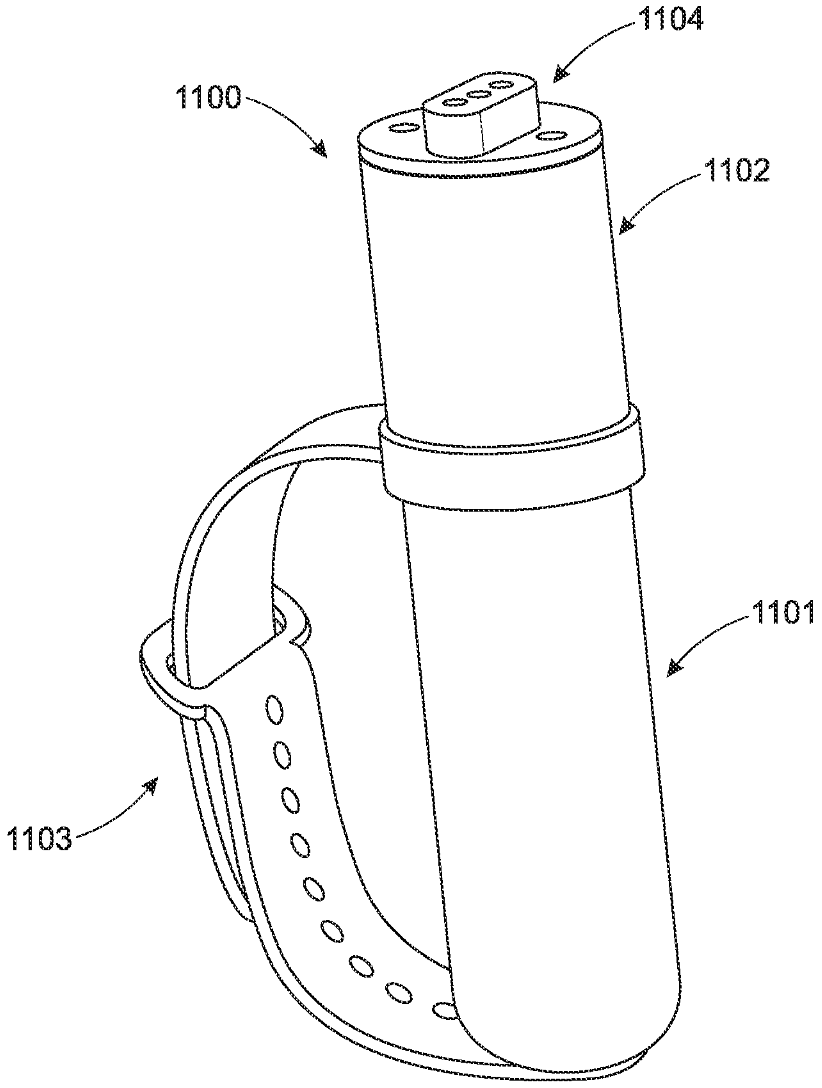
FIG. 1 shows a motion stabilizing device, according to an embodiment of the present disclosure.

FIG. 1 shows a conventional motion stabilizing device 1100, which serves as a base unit for receiving a cosmetic applicator according to an embodiment. The device 1100 includes a handle portion 1101, a receiver portion 1102, and a strap 1103. The receiver portion 1102 includes an interface 1104, shown as a male connector that couples with a cosmetic applicator, which will be discussed in detail below. The receiver portion could be utilized for communication between the base unit and the applicator. The connection to an adaptor and/or an applicator could be accomplished with a mechanical coupling, such as screw-in or snap-fit, or it could be accomplished with magnets.

Figure 2:
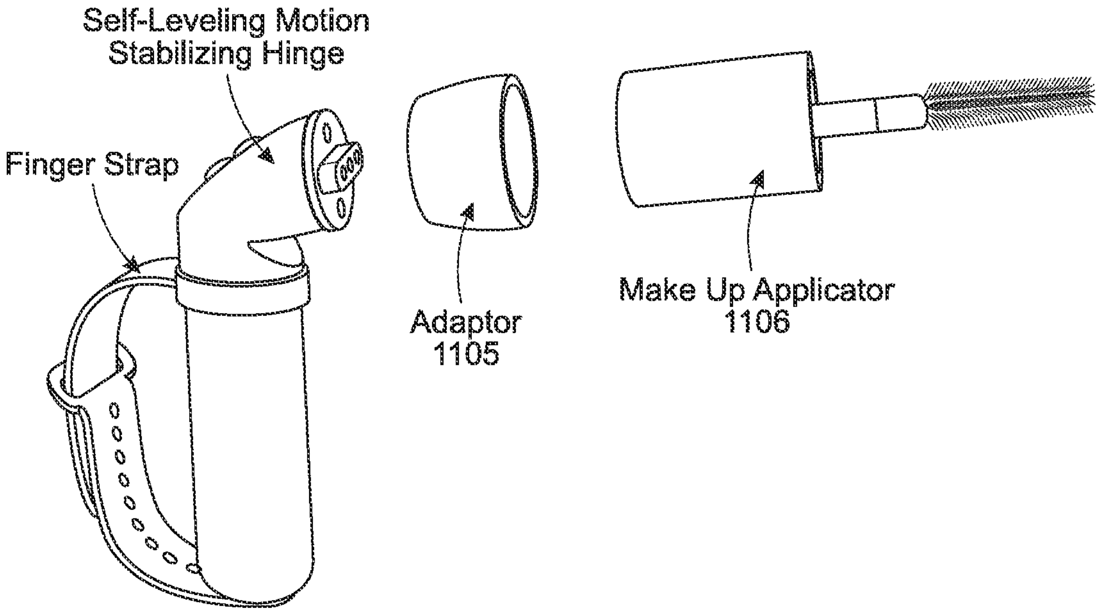
FIG. 2 shows how the motion stabilizing device couples with an adaptor and a make-up applicator, according to an embodiment of the present disclosure.

FIG. 2 shows how the device 1100 couples with an adaptor 1105 and a make-up applicator 1106. It can be seen that the adaptor fits over the exposed end of the receiver portion 1102. The adaptor includes electrical mating connectors (a female connector—not shown) in a recessed portion to make contact with the electric interface of the receiver portion 1101.

As shown in FIG. 2, the receiver portion 1102 is configured to contort, articulate, reposition, etc., between an upright posture (as shown in FIG. 1) and an angled posture (as shown in FIG. 2). This is accomplished with a hinge mechanism contained inside the receiver portion 1102. FIG. 2 shows that the hinge mechanism is a self-leveling/motion stabilizing hinge.

Figure 3A:
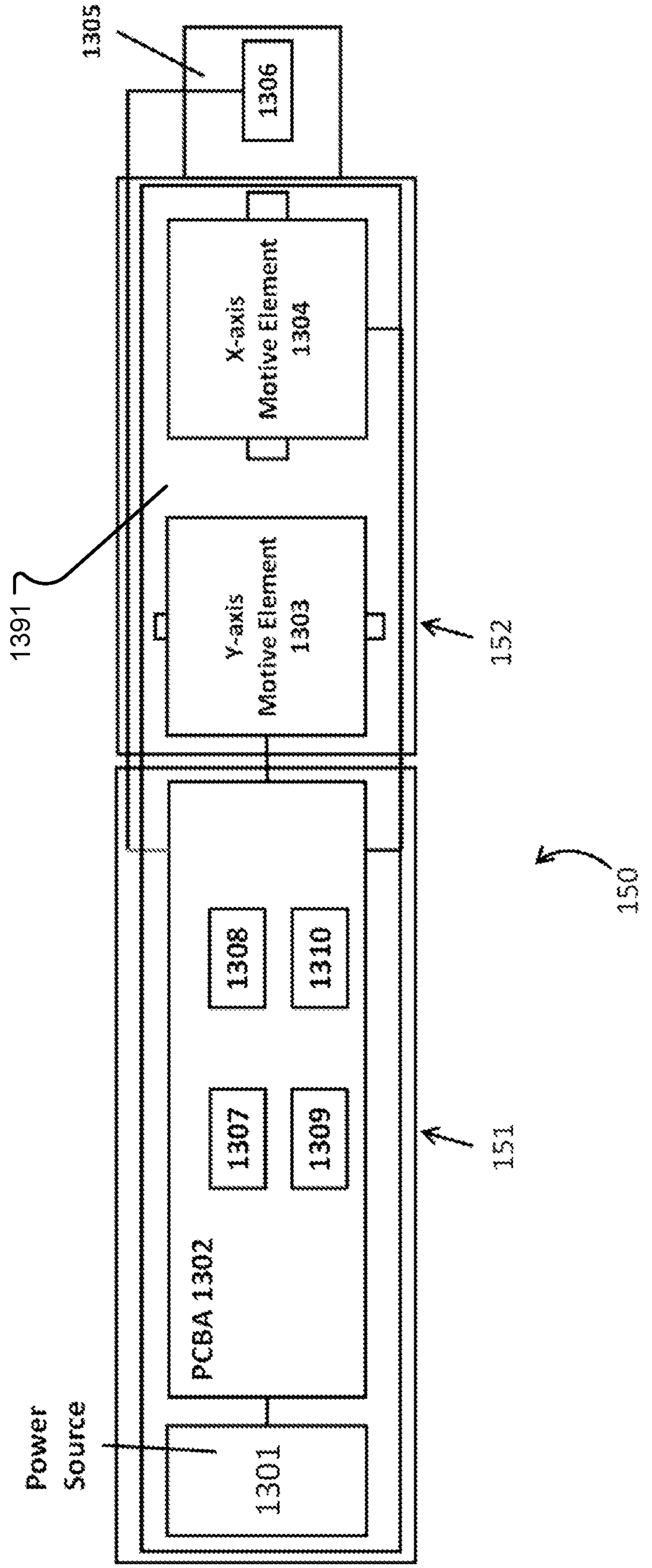
FIG. 3A shows a diagram of the internal components of a motion stabilizing, according to an embodiment of the present disclosure.

FIG. 3A shows a diagram of the internal components of device 1100 according to one embodiment. In the handle portion, the device includes a power source 1301, which may be a battery or the like. The device includes a printed circuit board assembly (PCBA) 1302, which may include positional sensor circuitry 1307, reader circuitry 1308, control circuitry 1309, and communication interface 1310, as understood in the art.

For instance, as the sensor circuitry 1307, the PCBA may include at least one inertial sensor and at least one distributed motion sensor to detect unintentional muscle movements and measure signals related to these unintentional muscle movements that are created when a user adversely affects motion of the applicator. These sensors also detect the motion of the stabilized output relative to device. The control circuitry sends voltage commands in response to the signals to the motion generating elements (described below) to cancel the user's tremors or unintentional muscle movements. This cancellation maintains and stabilizes a position of the applicator, keeping it stable.

One of ordinary skill in the art readily recognizes that a system and method in accordance with the present invention may utilize various implementations of the control circuitry and the sensor circuitry 1307 and that would be within the spirit and scope of the present invention. In one embodiment, the control circuitry 1309 comprises an electrical system capable of producing an electrical response from sensor inputs such as a programmable microcontroller or a field-programmable gate array (FPGA). In one embodiment, the control circuitry comprises an 8-bit ATMEGA8A programmable microcontroller manufactured by Atmel due to its overall low-cost, low-power consumption and ability to be utilized in high-volume applications.

In one embodiment, the at least one inertial sensor in the sensor circuitry 1307 is a sensor including but not limited to an accelerometer, gyroscope, or combination of the two. In one embodiment, the at least one distributed motion sensor in the sensor circuitry 1307 is a contactless position sensor including but not limited to a hall-effect magnetic sensor.

The system created by the combination of the sensor circuitry 1307, the control circuitry, and the motion generating elements may be a closed-loop control system that senses motion and acceleration at various points in the system and feeds detailed information into a control algorithm that moves the motion-generating elements appropriately to cancel the net effect of a user's unintentional muscle movements and thus stabilize the position of the applicator. The operation and details of the elements of the control system and control algorithm are understood in the art, as described in U.S. PG Publication 2014/0052275A1, incorporated herein by reference.

The communication interface 1310 may include a network controller such as BCM43342 Wi-Fi, Frequency Modulation, and Bluetooth combo chip from Broadcom, for interfacing with a network.

In the receiver portion of the device, there may be two motive elements to allow 3-dimensional movement of the receiver as anti-shaking movement. The two motive elements include a y-axis motive element 1303 and an x-axis motive element 1304, each being connected to and controlled by the PCBA 1302. Each of the motive elements may be servo motors as understood in the art. The device further includes end effector coupling 1305, which is configured to couple with the adaptor 1105. The end effector coupling 1305 may include a radiofrequency identification (RFID) reader 1306, configured to read an RFID tag, which may be included with the applicator, as will be discussed below.

Figure 3B:
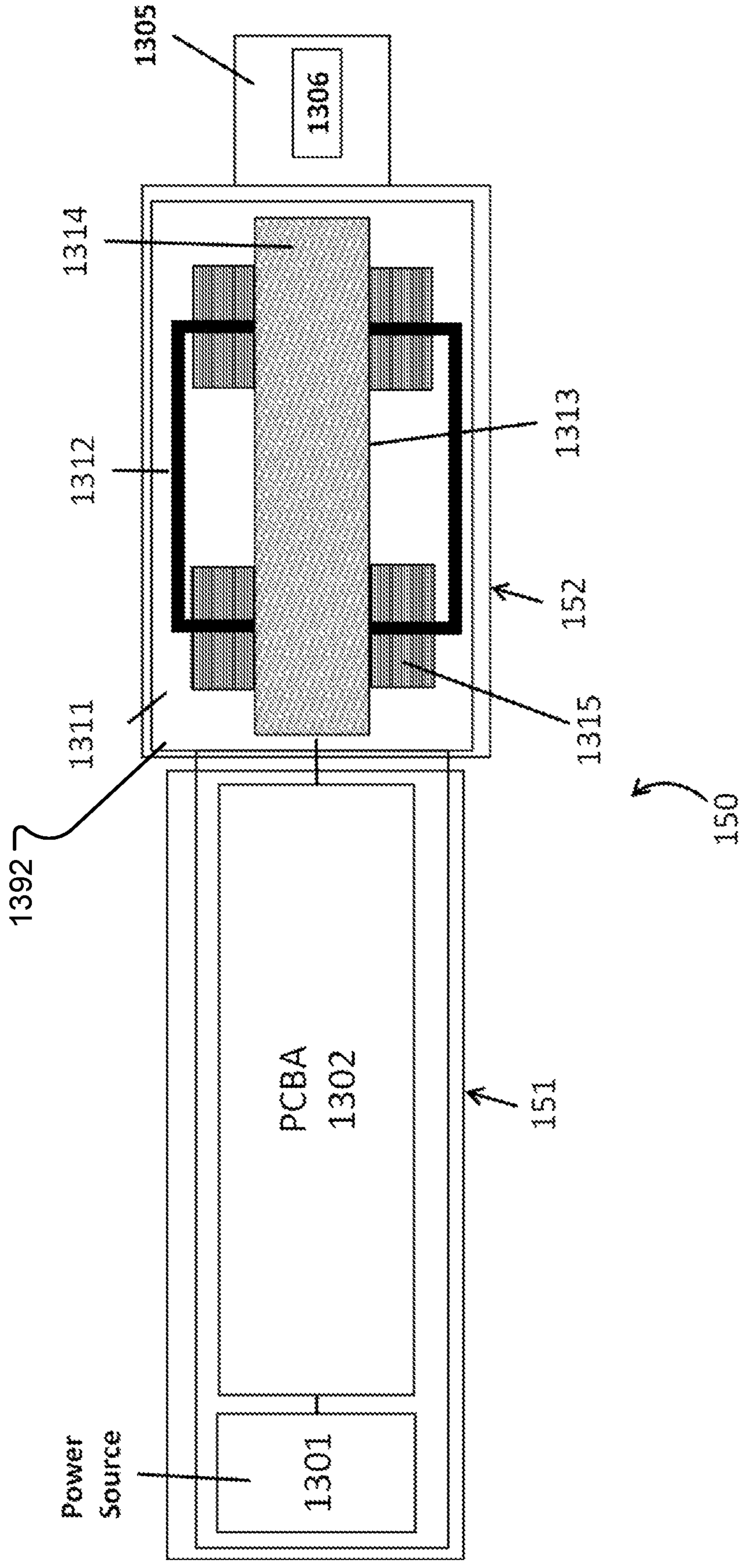
FIG. 3B shows a diagram of an alternative embodiment of the motion stabilizing device in which a receiver portion includes an electromagnetic positioner, according to an embodiment of the present disclosure.

FIG. 3B shows a diagram of an alternative embodiment of the device 1100 in which the receiver portion includes an electromagnetic positioner 1311 instead of the motive elements shown in FIG. 3A. The electromagnetic positioner 1311 may include U-shaped magnetic cores 1312 arrayed around a non-magnetic tube 1313, which is filled with a magnetic fluid 1314. Each of the magnetic cores has arm portions that are surrounded by windings 1315. The magnetic cores may be controlled by the control circuitry in the PCBA 1302 to act as a controllable active magnetic field-generating structure which is used to generate a variable magnetic field that acts upon the magnetic fluid, causing it to be displaced, thereby enabling the armature to be moved to a desired coordinate position and/or orientation. The details of implementing the electromagnetic positioner 1311 may be found in U.S. Pat. No. 6,553,161, which is incorporated herein by reference.

In one embodiment, the present disclosure is directed towards a cosmetic applicator. The cosmetic applicator can be used for a variety of cosmetics and cosmetic applications, including, but not limited to, mascara, eyeliner, eyebrow products, lip products (lipstick, lip gloss, lip liner, etc.), skin products, and/or hair products. In one embodiment, the cosmetic applicator can include an adapter, wherein the adapter can connect the cosmetic applicator to a motion stabilizer. The motion stabilizer can be, for example, a handle that can counteract unintentional motions such as tremors or spasms. These motions can interfere with the application of cosmetics and can also make it difficult to generally interact with cosmetic applicators or tools. For example, the many cosmetic products require a twisting motion or force to be applied to open or extrude the product. It can be difficult for users to achieve the range of motion or the precision necessary to apply these forces to the cosmetic. In one embodiment, the cosmetic applicator can hold a cosmetic and can enable the proper force to be applied to the cosmetic to open, close, mix, stir, blend, extrude, or achieve other similar functions necessary for application.

Figure 4:
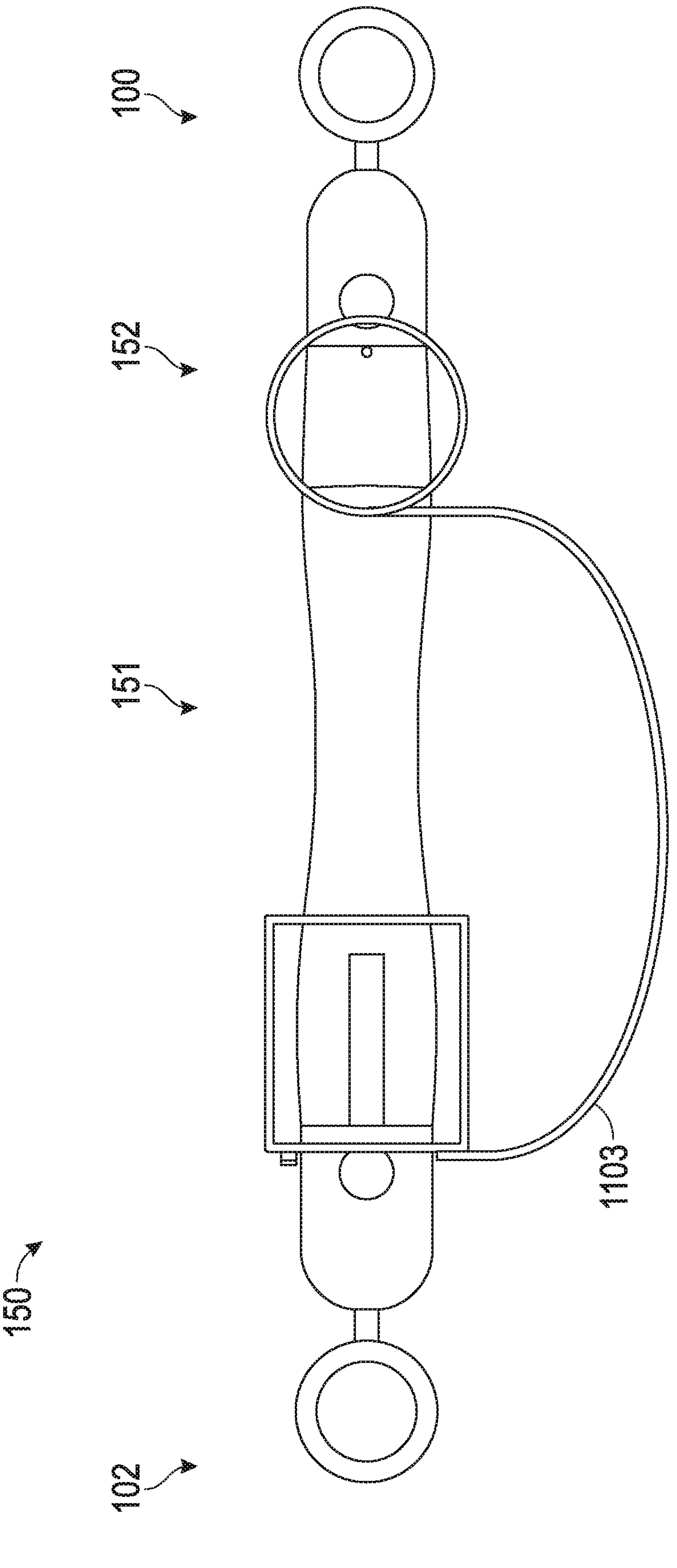
FIG. 4 shows an overview of a universal adapter handle connection system, according to an embodiment of the present disclosure.

FIG. 4 shows an overview of a cosmetic securement device including a motion stabilizer device 150, a first cosmetic adapter 100, and a second cosmetic adapter 102, according to one embodiment of the present disclosure. The motion stabilizer device 150 can include a handle portion 151 and a hinge portion 152 (receiver portion) at a first end of the handle portion 151 with the first cosmetic adapter 100 attached to the hinge portion 152 at the first end of the handle portion 151 and the second cosmetic adapter 102 attached to the handle portion 151 at a second end of the handle portion 151. In an embodiment, the handle portion 151 is functionally similar to the handle portion 1101 shown in FIG. 1. The receiver portion 152 can be functionally similar to the receiver portion 1102 shown in FIG. 1. The basic features and operation of the cosmetic securement device of FIG. 4 are described in co-pending U.S. patent application Ser. Nos. 18/091,882; 18/091,920; 18/091,843; 18/091,925; 18/148,957; and Ser. No. 18/148,880; and Ser. No. 18/148,930, which are incorporated herein by reference.

In an embodiment, the motion stabilizer device 150 as a whole is referred to as a motion stabilizer handle. In an embodiment, the cosmetic securement device includes a first cosmetic adapter 100, wherein the first cosmetic adapter 100 is coupled to the receiver portion 152 of the motion stabilizer device 150. In an embodiment, the first cosmetic adapter 100 is configured to hold a cosmetic tool or product. In one embodiment, the first cosmetic adapter 100 comprises a universal adapter configured to hold different types of cosmetic products. For example, the first cosmetic adapter 100 can include a ring-shaped holder (as shown). Various configurations of the first cosmetic adapter 100 can be used for different cosmetics and tools. For example, the shape and dimensions of the cosmetic holder can be configured for different cosmetic products. The first cosmetic adapter 100 can be easily attached to and removed from the motion stabilizer device.

In an embodiment, the cosmetic securement device can include the second cosmetic adapter 102, wherein the second cosmetic adapter 102 can be coupled to the handle portion 151 or to another of the receiver portion 152 of the motion stabilizer device 150 disposed at the second end of the handle portion 151. Additionally or alternatively, the second cosmetic adapter 102 is formed as part of the second end of the handle portion 151. The second cosmetic adapter 102 can also hold a cosmetic tool or product. In one embodiment, the second cosmetic adapter 102 is a universal adapter configured to hold different types of cosmetic products. For example, the second cosmetic adapter 102 can include a ring-shaped holder (as shown). Various configurations of the second cosmetic adapter 102 can be used for different cosmetics and tools. For example, the shape and dimensions of the cosmetic holder can be configured for different cosmetic products. The second cosmetic adapter 102 can be easily attached to and removed from the motion stabilizer device 150.

In one embodiment, the first cosmetic adapter 100 is coupled to the receiver portion 152 of the motion stabilizer device 150 via a magnetic attachment. The base or bottom end of the first cosmetic adapter 100 can form a chamber that can fit over a projection at the tip of the receiver portion 152. The base of the adapter can include at least one magnet, wherein the at least one magnet can be attracted to and attach to a magnet in the receiver portion 152. In one embodiment, the chamber formed at the base of the first cosmetic adapter 100 can fit over the receiver portion 152 in more than one orientation. The chamber can be a hollow area within the body of the adapter that is fully contained by the walls of the first cosmetic adapter 100. The chamber can be approximately conical in shape.

In an embodiment, the chamber is cylindrical. The chamber can be configured to fit over a projection on one end of the motion stabilizer. The chamber can be used to align and guide the attachment of the cosmetic applicator to the motion stabilizer. The fit of the chamber over and around the projection on the end of the motion stabilizer limits lateral motion that would misalign the cosmetic applicator and the motion stabilizer. It can be easier for a user to align the chamber over the end of the motion stabilizer than it would be for the user to align the edges of a circular face of the adapter with the edges of a circular face of the motion stabilizer. The chamber can have rotational symmetry such that the cutout can be placed over the end of the motion stabilizer in any orientation or at any degree of rotation around the axis of the chamber. In one embodiment, the bottom end of the adapter body can include additional physical structures that can align, guide, and fix the adapter to the motion stabilizer.

In one embodiment, one or more motion stabilization components is placed in an internal sleeve, wherein the internal sleeve can be inserted into the motion stabilizer device 150. In one embodiment, the motion stabilizer device 150 can be a hollow shell (e.g., cylindrical shell), and the internal sleeve containing motion stabilization components can be a cylindrical sleeve with a diameter that is smaller than the diameter of the motion stabilizer device 150. The motion stabilization components can be located in the internal sleeve can be located in alignment with the positions illustrated in FIG. 3A and FIG. 3B.

In one embodiment, the internal sleeve can form a receptacle for one or more motion stabilization components. For example, the internal sleeve can form cutouts along the length of the sleeve, the cutouts being sized for the one or more motion stabilization components. Each motion stabilization component can be placed or embedded in a cutout to be secured in the internal sleeve. In one embodiment, the internal sleeve comprises a hollow cylinder, wherein motion stabilization components can be placed inside the hollow cylinder. The internal sleeve can enable placement of the motion stabilization components in the motion stabilizer device and removal of the motion stabilizer components from the motion stabilizer device as needed. In one embodiment, the cosmetic securement device can include a locking mechanism and/or an eject mechanism to secure and release the internal sleeve and the motion stabilizer components contained therein.

In one embodiment, the motion stabilizer device 150 can include at least two cosmetic adapters. Different disabilities can require a different kind of handle per disability. Thus, a single device that will work for disabilities of both limited mobility of hands/arms as well as for tremor-based disabilities can be desired.

Figure 5:
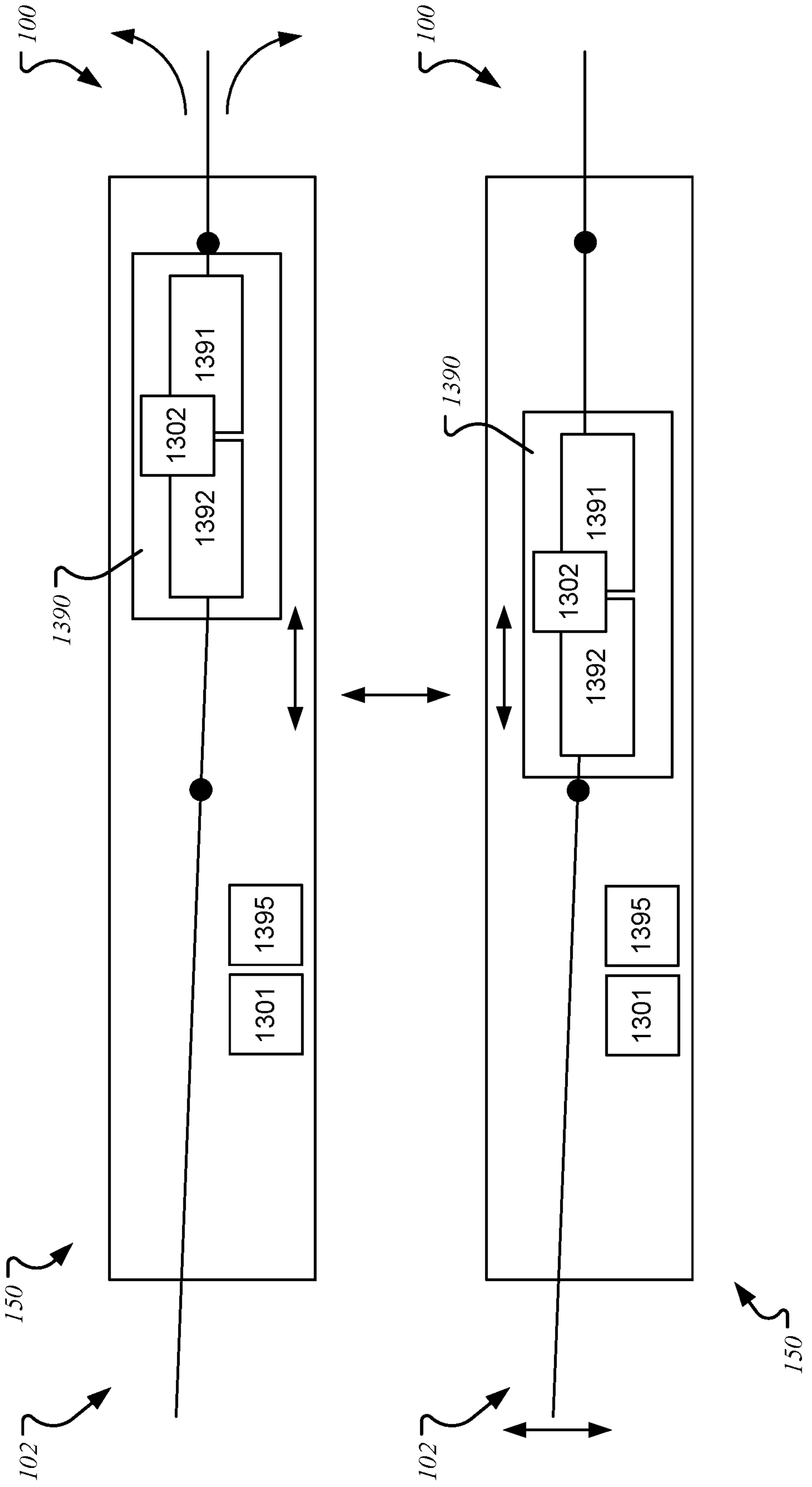
FIG. 5 shows a schematic of a cosmetic securement device including a motion stabilizer device, a first cosmetic adapter, and a second cosmetic adapter, according to an embodiment of the present disclosure.

FIG. 5 shows a schematic of a multi-configuration cosmetic applicator, according to an embodiment of the present disclosure. In an embodiment, the motion stabilizer device 150 can include multiple motion adjustment groups configured to control motion of respective cosmetic adapters. For example, the y-axis motive element 1303 and the x-axis motive element 1304 can be included in a first motion adjustment group 1391 and the electromagnetic positioner 1311 can be included in a second motion adjustment group 1392. The first motion adjustment group 1391 controls motion of, for example, the first cosmetic adapter 100 and the hinge portion 152 at the first end of the handle portion 151. The second motion adjustment group 1392 controls motion of, for example, the second cosmetic adapter 102 at the second end of the handle portion 151. In general, the first motion adjustment group 1391 and the second motion adjustment group 1392 include motive elements as previously described that control motion of the attached cosmetic adapter, such as mechanical or magnetic motive elements. The PCBA 1302 is electrically connected to the first motion adjustment group 1391 and the second motion adjustment group 1392 to control the first motion adjustment group 1391 and the second motion adjustment group 1392.

In an embodiment, the PCBA 1302, the first motion adjustment group 1391, and the second motion adjustment group 1392 are included in an adjustable coupler 1390 configured to be reversibly adjusted inside the motion stabilizer device 150 between at least two coupling arrangements. The desired arrangement can be determined by, for example, an accelerometer or gyroscope of the sensor circuitry 1307 of the PCBA 1302. In an embodiment, the user grasps the motion stabilizer device 150 and arranges the motion stabilizer device 150 vertically such that the first end of the handle portion 151 is disposed vertically over the second end of the handle portion 151. The accelerometer or gyroscope detects the motion and determines the resulting orientation of the motion stabilizer device 150.

In an embodiment, based on the arrangement of the first end of the handle portion 151 over the second end of the handle portion 151, the PCBA 1302 determines that the user desires to use the first cosmetic adapter 100 and therefore needs to use the first motion adjustment group 1391. To couple the first motion adjustment group 1391 to the first cosmetic adapter 100, the motion stabilizer device 150 automatically adjusts the adjustable coupler 1390 via, for example, a motor 1395 disposed in the motion stabilizer device 150. The motor 1395 can be electrically connected to the PCBA 1302. That is, the PCBA 1302, upon determining the arrangement of the motion stabilizer device 150 calls for the use of the first cosmetic adapter 100, transmits a signal to the motor 1395 to translate the coupler 1390 towards the hinge portion 152 and the first cosmetic adapter 100, and the adjustable coupler 1395 couples to the hinge portion 152 and the first cosmetic adapter 100. For example, the first motion adjustment group 1391 couples to the hinge portion 152 and the first cosmetic adapter 100.

In an embodiment, when coupled with the first cosmetic adapter 100, the PCBA 1302 is configured to control the first motion adjustment group 1391 in order to manipulate the first cosmetic adapter 100. For example, the PCBA 1302 and the sensor circuitry 1307 sense motion and acceleration at various points in the system and feeds detailed information into the control algorithm that moves the first motion adjustment group 1391 to cancel the net effect of a user's unintentional muscle movements and thus stabilize the position of the first cosmetic adapter 100 (top of FIG. 5).

In an embodiment, based on the arrangement, the PCBA 1302 determines that the user desires to use the second cosmetic adapter 102 and therefore needs to use the second motion adjustment group 1392. For example, the PCBA 1302 determines that the first end of the handle portion 151 is disposed vertically under the end with second end of the handle portion 152. To couple the second motion adjustment group 1392 to the second cosmetic adapter 102, the motion stabilizer device 150 can automatically adjust the adjustable coupler 1390 via, for example, the motor 1395. That is, the PCBA 1302, upon determining the arrangement of the motion stabilizer device 150 calls for the use of the second cosmetic adapter 102, transmits a signal to the motor 1395 to translate the coupler 1390 towards the second cosmetic adapter 102 disposed at the second end of the handle portion 151 and the adjustable coupler 1395 couples to the second cosmetic adapter 102.

In an embodiment, when coupled with the second cosmetic adapter 102, the PCBA 1302 is configured to control the second motion adjustment group 1392 in order to manipulate the second cosmetic adapter 102. For example, the PCBA 1302 and the sensor circuitry 1307 sense motion and acceleration at various points in the system and feeds detailed information into the control algorithm that control the magnetic cores of the second motion adjustment group 1392. This results in the controllable active magnetic field-generating structure which is used to generate the variable magnetic field that acts upon the magnetic fluid, causing it to be displaced, thereby enabling the second cosmetic adapter 102 to be moved to the desired coordinate position and/or orientation (bottom of FIG. 5).

In an embodiment, the RFID reader 1306, which can be disposed at both ends of the motion stabilizer device 150, can detect which of the cosmetic adapters is installed at the end the user is trying to use. For example, the motion stabilizer device 150 can be arranged such that the first end of the handle portion 151 is arranged vertically over the second end of the handle portion 151, which would normally indicate that the user is attempting to use the first cosmetic adapter 100 with the hinge portion 152 and the y-axis motive element 1303 and the x-axis motive element 1304 for users with limited arm mobility. However, the user can instead attach the second cosmetic adapter 102 to the hinge portion 152 (e.g., on the end effector coupling 1305), which is detected by the RFID reader 1306. Upon detecting and determining the second cosmetic adapter 102 is attached to the hinge portion 152, the RFID reader 1306 transmits a signal to the PCBA 1302, and the PCBA 1302 transmits a signal to the motor 1395 to translate the adjustable coupler 1390 towards the first end of the handle portion 151 to couple the adjustable coupler 1390 to the hinge portion 152 and the second cosmetic adapter 102 and therefore instead use the second motion adjustment group 1392 to control the second cosmetic adapter 102.

In an embodiment, the PCBA 1302 is communicatively coupled to a remote processing device and configured to update the remote processing device with regards to the arrangement of the motion stabilizer device 150. In an embodiment, the remote processing device is configured to receive data from the PCBA 1302 and transmit instructions to the PCBA 1302 based on the arrangement of the motion stabilizer device 150. In an embodiment, the remote processing device is configured to receive input from the user regarding arrangement settings, such as a threshold for a rotation or orientation of the motion stabilizer device 150 before instructing the PCBA 1302 to adjust the adjustable coupler 1390.

Figure 6:
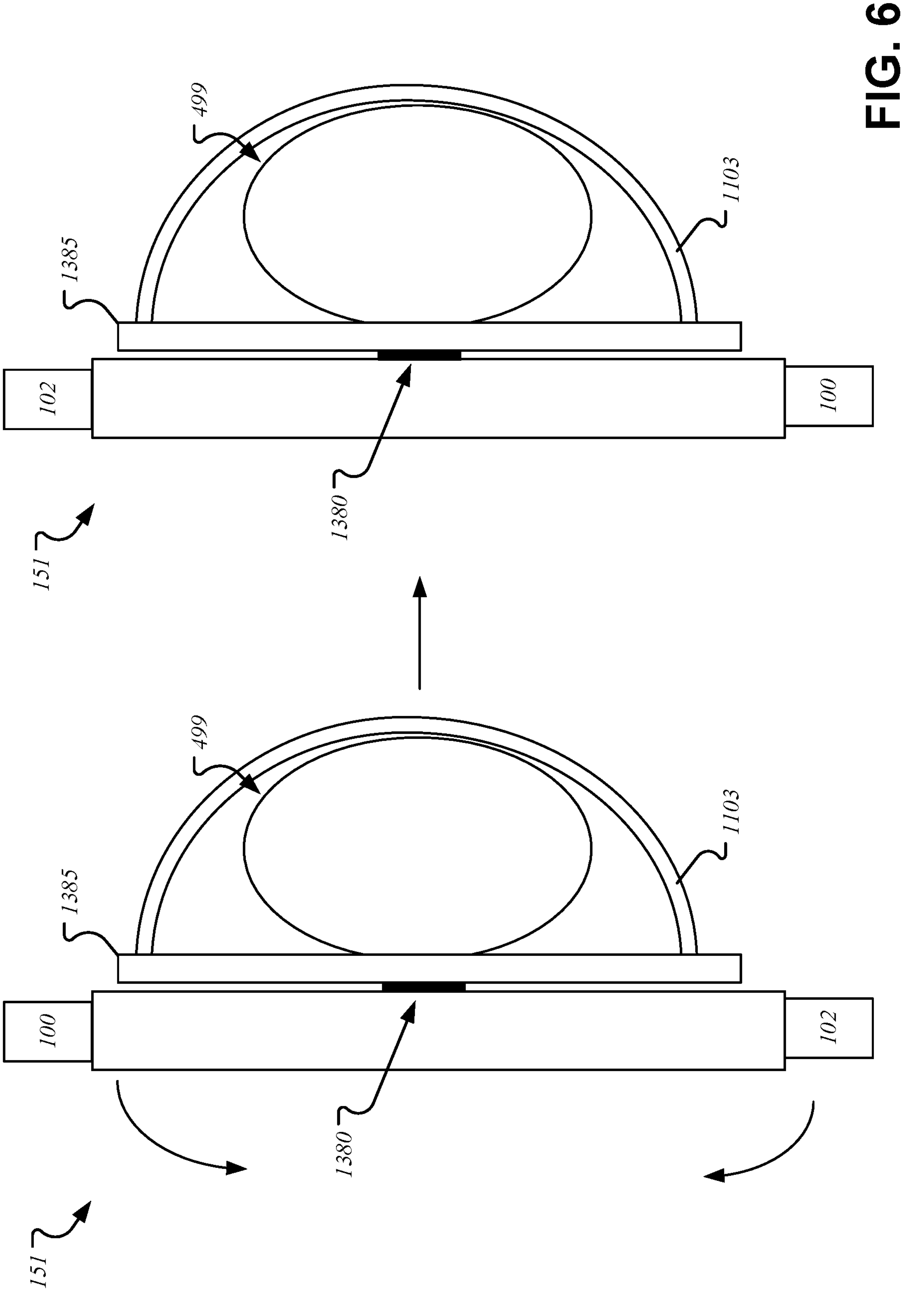
FIG. 6 shows a schematic of a rotating platform for the strap for the multi-configuration cosmetic applicator, according to an embodiment of the present disclosure.

FIG. 6 shows a schematic of a rotating platform 1385 for the strap 1103 for the multi-configuration cosmetic applicator, according to an embodiment of the present disclosure. In an embodiment, the user can desire to quickly change between the first cosmetic adapter 100 and the second cosmetic adapter 102 without needing to unsecure the strap 1103 from a hand 499 inserted in the strap 1103, flip the motion stabilizer device 150 so the desired end is arranged properly, and then re-secure the strap 1103 around the hand 499. Thus, the motion stabilizer device 150 can include the rotating platform 1385 that is attached to the motion stabilizer device 150, for example along the handle portion 151, via a post 1380 configured to allow rotation of the rotating platform 1385 (or by extension, rotation of the motion stabilizer device 150 with the rotating platform 1385 held stationary).

As shown, the second cosmetic adapter 102 is arranged vertically below the first cosmetic adapter 100 on the left of FIG. 6. Upon finishing the use of the first cosmetic adapter 100, the user can rotate the motion stabilizer device 150 about the post 1380 while holder the user's hand 499 still until the second cosmetic adapter 102 is arranged vertically over the first cosmetic adapter 100 to allow the user to use the second cosmetic adapter 102. As previously described, this re-arrangement can be detected by the PCBA 1302, which adjusts the adjustable coupler 1390 according to the change in desired adapter.

In one embodiment, the present disclosure relates to a device adjustment system for a cosmetic device configured for users with limited mobility, including a motion stabilizer handle; a first cosmetic adapter attached to a first end of the motion stabilizer handle; a second cosmetic adapter attached to a second end of the motion stabilizer handle; and an adjustable coupler disposed in the motion stabilizer handle, the adjustable coupler including a first motion adjustment group, a second motion adjustment group, and processing circuitry, the adjustable coupler being adjustably translated between the first end and the second end of the motion stabilizer handle, the first motion adjustment group configured to couple with the first cosmetic adapter and manipulate a motion of the first cosmetic adapter, the second motion adjustment group configured to couple with the second cosmetic adapter and manipulate a motion of the second cosmetic adapter, the processing circuitry configured to determine an arrangement of the motion stabilizer handle and instruct a motor disposed in the motion stabilizer handle and mechanically connected to the adjustable coupler to adjust a coupling of the adjustable coupler based on the arrangement of the motion stabilizer handle.

In an embodiment, the device further includes a hinge portion attached to the first end of the motion stabilizer handle, the first cosmetic adapter being attached to the hinge portion at the first end of the motion stabilizer handle.

In an embodiment, the first motion adjustment group includes an x-axis motive element and a y-axis motive element configured to maintain a level position of the first cosmetic adapter in response to manipulation of the motion stabilizer handle that arranges the motion stabilizer handle in a non-level arrangement.

In an embodiment, the second motion adjustment group includes an electromagnetic positioner configured to maintain a same position of the second cosmetic adapter in free space in response to manipulation of the motion stabilizer handle with random oscillating motions.

In an embodiment, the electromagnetic positioner includes magnetic cores arrayed around a non-magnetic tube filled with a magnetic fluid, each of the magnetic cores surrounded by windings, the magnetic cores controlled via the processing circuitry to generate a variable magnetic field that acts upon and displaces the magnetic fluid to adjust the second cosmetic adapter.

In an embodiment, upon coupling the adjustable coupler to the first cosmetic adapter, the adjustable coupler is not coupled to the second cosmetic adapter.

In an embodiment, the processing circuitry is configured to upon determining the first end of the motion stabilizer handle is vertically elevated compared to the second end of the motion stabilizer handle and the first cosmetic adapter is attached to the first end of the motion stabilizer handle, instruct the motor to adjust the adjustable coupler towards the first end of the motion stabilizer handle to couple the first motion adjustment group with the first cosmetic adapter.

In an embodiment, the processing circuitry is configured to upon determining the second end of the motion stabilizer handle is vertically elevated compared to the first end of the motion stabilizer handle and the second cosmetic adapter is attached to the second end of the motion stabilizer handle, instruct the motor to adjust the adjustable coupler towards the second end of the motion stabilizer handle to couple the second motion adjustment group with the second cosmetic adapter.

In an embodiment, the processing circuitry is configured to upon determining the first end of the motion stabilizer handle is vertically elevated compared to the second end of the motion stabilizer handle and the second cosmetic adapter is attached to the first end of the motion stabilizer handle via a radiofrequency identification (RFID) reader disposed at the second end of the motion stabilizer handle, instruct the motor to adjust the adjustable coupler towards the first end of the motion stabilizer handle to couple the second motion adjustment group with the second cosmetic adapter.

In an embodiment, the device further includes a strap attached to a rotating platform, the rotating platform connected to the motion stabilizer handle via a rotating post, a rotation axis of the rotating post being orthogonal to a length axis of the motion stabilizer handle, the strap configured to secure an object to the rotating platform and the motion stabilizer handle.

In an embodiment, the adjustable coupler includes an accelerometer electrically connected to the processing circuitry.

In an embodiment, the adjustable coupler includes a gyroscope electrically connected to the processing circuitry.

Obviously, numerous modifications and variations of the present invention are possible in light of the above teachings. It is therefore to be understood that within the scope of the appended claims, the invention may be practiced otherwise than as specifically described herein.

The invention claimed is:

1. A device adjustment system for a cosmetic device configured for users with limited mobility, comprising:

a motion stabilizer handle;

a first cosmetic adapter attached to a first end of the motion stabilizer handle;

a second cosmetic adapter attached to a second end of the motion stabilizer handle; and an adjustable coupler disposed in the motion stabilizer handle, the adjustable coupler including a first motion adjustment group, a second motion adjustment group, and processing circuitry, the adjustable coupler being adjustably translated between the first end and the second end of the motion stabilizer handle, the first motion adjustment group configured to couple with the first cosmetic adapter and manipulate a motion of the first cosmetic adapter, the second motion adjustment group configured to couple with the second cosmetic adapter and manipulate a motion of the second cosmetic adapter, the processing circuitry configured to determine an arrangement of the motion stabilizer handle and instruct a motor disposed in the motion stabilizer handle and mechanically connected to the adjustable coupler to adjust a coupling of the adjustable coupler based on the arrangement of the motion stabilizer handle.

2. The device of claim 1, further comprising a hinge portion attached to the first end of the motion stabilizer handle, the first cosmetic adapter being attached to the hinge portion at the first end of the motion stabilizer handle.

3. The device of claim 2, wherein the first motion adjustment group includes an x-axis motive element and a y-axis motive element configured to maintain a level position of the first cosmetic adapter in response to manipulation of the motion stabilizer handle that arranges the motion stabilizer handle in a non-level arrangement.

4. The device of claim 1, wherein the second motion adjustment group includes an electromagnetic positioner configured to maintain a same position of the second cosmetic adapter in free space in response to manipulation of the motion stabilizer handle with random oscillating motions.

5. The device of claim 4, wherein the electromagnetic positioner includes magnetic cores arrayed around a non-magnetic tube filled with a magnetic fluid, each of the magnetic cores surrounded by windings, the magnetic cores controlled via the processing circuitry to generate a variable magnetic field that acts upon and displaces the magnetic fluid to adjust the second cosmetic adapter.

6. The device of claim 1, wherein upon coupling the adjustable coupler to the first cosmetic adapter, the adjustable coupler is not coupled to the second cosmetic adapter.

7. The device of claim 1, wherein the processing circuitry is configured to upon determining the first end of the motion stabilizer handle is vertically elevated compared to the second end of the motion stabilizer handle and the first cosmetic adapter is attached to the first end of the motion stabilizer handle, instruct the motor to adjust the adjustable coupler towards the first end of the motion stabilizer handle to couple the first motion adjustment group with the first cosmetic adapter.

8. The device of claim 1, wherein the processing circuitry is configured to upon determining the second end of the motion stabilizer handle is vertically elevated compared to the first end of the motion stabilizer handle and the second cosmetic adapter is attached to the second end of the motion stabilizer handle, instruct the motor to adjust the adjustable coupler towards the second end of the motion stabilizer handle to couple the second motion adjustment group with the second cosmetic adapter.

9. The device of claim 1, wherein the processing circuitry is configured to upon determining the first end of the motion stabilizer handle is vertically elevated compared to the second end of the motion stabilizer handle and the second cosmetic adapter is attached to the first end of the motion stabilizer handle via a radiofrequency identification (RFID) reader disposed at the second end of the motion stabilizer handle, instruct the motor to adjust the adjustable coupler towards the first end of the motion stabilizer handle to couple the second motion adjustment group with the second cosmetic adapter.

10. The device of claim 1, further comprising a strap attached to a rotating platform, the rotating platform connected to the motion stabilizer handle via a rotating post, a rotation axis of the rotating post being orthogonal to a length axis of the motion stabilizer handle, the strap configured to secure an object to the rotating platform and the motion stabilizer handle.

11. The device of claim 1, wherein the adjustable coupler includes an accelerometer electrically connected to the processing circuitry.

12. The device of claim 1, wherein the adjustable coupler includes a gyroscope electrically connected to the processing circuitry.

13. A method of adjusting an adjustable coupler in a cosmetic device configured for users with limited mobility, comprising:

determining, via processing circuitry disposed in a motion stabilizer handle of the cosmetic device, an arrangement of the motion stabilizer handle, the motion stabilizer handle including a first cosmetic adapter attached to a first end of the motion stabilizer handle and a second cosmetic adapter attached to a second end of the motion stabilizer handle, the adjustable coupler including a first motion adjustment group, a second motion adjustment group, and the processing circuitry, the adjustable coupler being adjustably translated between the first end and the second end of the motion stabilizer handle, the first motion adjustment group configured to couple with the first cosmetic adapter and manipulate a motion of the first cosmetic adapter, the second motion adjustment group configured to couple with the second cosmetic adapter and manipulate a motion of the second cosmetic adapter, the processing circuitry configured to determine an arrangement of the motion stabilizer handle and instruct a motor disposed in the motion stabilizer handle and mechanically connected to the adjustable coupler to adjust a coupling of the adjustable coupler based on the arrangement of the motion stabilizer handle; and upon determining the first end of the motion stabilizer handle is vertically elevated compared to the second end of the motion stabilizer handle and the first cosmetic adapter is attached to the first end of the motion stabilizer handle, instruct, via the processing circuitry, the motor to adjust the adjustable coupler towards the first end of the motion stabilizer handle to couple the first motion adjustment group with the first cosmetic adapter.

14. The method of claim 13, further comprising upon determining the second end of the motion stabilizer handle is vertically elevated compared to the first end of the motion stabilizer handle and the second cosmetic adapter is attached to the second end of the motion stabilizer handle, instruct, via the processing circuitry, the motor to adjust the adjustable coupler towards the second end of the motion stabilizer handle to couple the second motion adjustment group with the second cosmetic adapter.

15. The method of claim 13, further comprising upon determining the first end of the motion stabilizer handle is vertically elevated compared to the second end of the motion stabilizer handle and the second cosmetic adapter is attached to the first end of the motion stabilizer handle via a radiofrequency identification (RFID) reader disposed at the second end of the motion stabilizer handle, instruct, via the processing circuitry, the motor to adjust the adjustable coupler towards the first end of the motion stabilizer handle to couple the second motion adjustment group with the second cosmetic adapter.

16. The method of claim 13, wherein the motion stabilizer handle includes a hinge portion attached to the first end of the motion stabilizer handle, the first cosmetic adapter being attached to the hinge portion at the first end of the motion stabilizer handle.

17. The method of claim 16, wherein the first motion adjustment group includes an x-axis motive element and a y-axis motive element configured to maintain a level position of the first cosmetic adapter in response to manipulation of the motion stabilizer handle that arranges the motion stabilizer handle in a non-level arrangement.

18. The method of claim 13, wherein the second motion adjustment group includes an electromagnetic positioner configured to maintain a same position of the second cosmetic adapter in free space in response to manipulation of the motion stabilizer handle with random oscillating motions.

19. The method of claim 13, wherein the adjustable coupler includes an accelerometer electrically connected to the processing circuitry, and the processing circuitry is further configured to determine the arrangement of the motion stabilizer handle via the accelerometer.

20. The method of claim 13, wherein the adjustable coupler includes a gyroscope electrically connected to the processing circuitry, and the processing circuitry is further configured to determine the arrangement of the motion stabilizer handle via the gyroscope.

* * * * *